United States Patent [19]

Munk

[11] Patent Number: 4,457,846

[45] Date of Patent: Jul. 3, 1984

[54] LIQUID CHROMATOGRAPHY METHODS AND DEVICES

[75] Inventor: Miner N. Munk, Riviera Beach, Fla.

[73] Assignee: Milton Roy Company, St. Petersburg, Fla.

[21] Appl. No.: 396,389

[22] Filed: Jul. 8, 1982

[51] Int. Cl.³ .............................................. B01D 15/08
[52] U.S. Cl. ................................. 210/656; 210/198.2; 210/321.1
[58] Field of Search ........................... 55/67, 197, 386; 210/198.2, 656, 321.1

[56] References Cited

U.S. PATENT DOCUMENTS

| 3,346,486 | 10/1967 | Winter et al. | 210/198.2 |
| 3,692,669 | 9/1972 | Bauman | 210/198.2 |
| 4,309,286 | 1/1982 | Lenihan et al. | 210/198.2 |
| 4,350,595 | 9/1982 | Gunkel | 210/198.2 |
| 4,354,932 | 10/1982 | McNeil | 210/198.2 |

OTHER PUBLICATIONS

Gas Chromatography with Glass Capillary Columns by Jennings, Academic Press of New York, p. 49, 1978.

*Primary Examiner*—John Adee
*Attorney, Agent, or Firm*—Carroll F. Palmer

[57] ABSTRACT

In the analysis of substances by liquid chromatography, samples to be analyzed are introduced into the chromatography column by being loaded into a fluid permeable section in a cartridge, placing the sample loaded section over the inlet end of the column and flowing solvent through such section into the column. The cartridge may be a plate with an opening through it with the ends of the opening covered by permeable membranes or the opening may be packed with porous material. The cartridge may have a plurality of such openings and these may be in the form of a line on a rectangular plate or a circle on a circular plate. The new methods and devices of the invention are particularly useful in micro-scale liquid chromatographic procedures.

22 Claims, 11 Drawing Figures

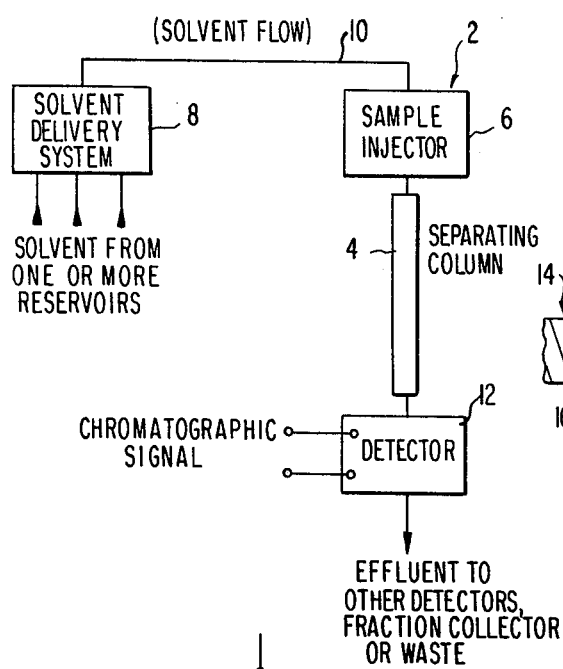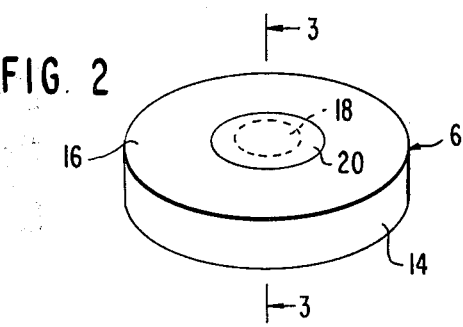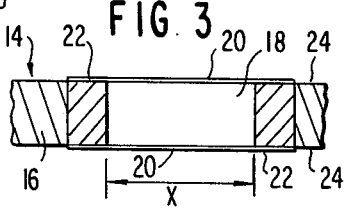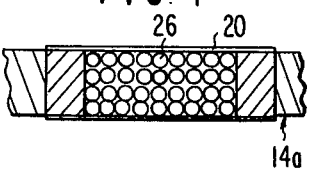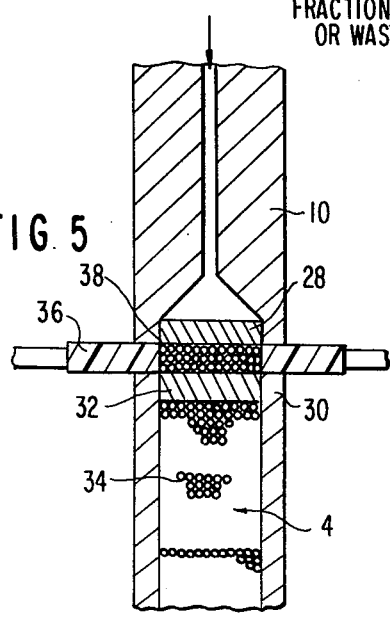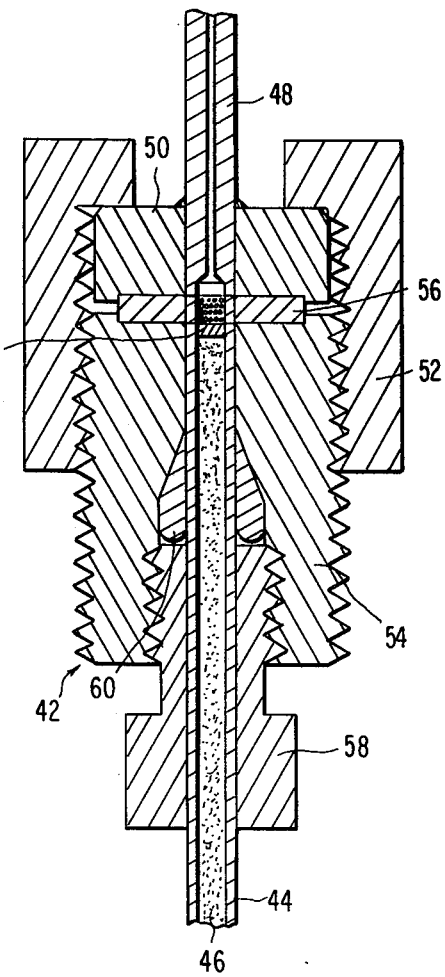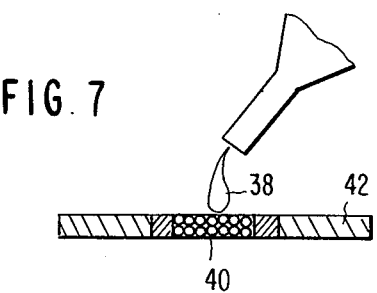

LIQUID CHROMATOGRAPHY METHODS AND DEVICES

BACKGROUND OF THE INVENTION

1. Field of the Invention

This invention relates broadly to liquid chromatography methods and devices. More particularly, it concerns methods and devices to introduce substance samples into the chromatography column and especially in micro-scale chromatography procedures.

2. Description of the Prior Art

Conventional methods for introducing a sample into a liquid chromatograph include injection of the sample by a syringe near the inlet of the column or the valve switching of a sample loaded loop into the flow stream ahead of the column. Such methods can limit the chromatographic efficiency of the analysis, especially in micro-scale liquid chromatography. For example, syringe introduction of the sample into the solvent filled space ahead of the column causes dispersion of the sample into the neighboring solvent and causes spreading of the chromatographic peaks. On the other hand, syringe introduction into the column bed results in a non-uniform concentration profile and frequent plugging of the syringe needle with resulting peak spreading and nonrepeatable quantity of introduced sample.

With valve switching of a sample loaded loop into the flow stream, this inevitably results in dispersion of the sample in the solvent and broadened chromatogrpahic peaks. This dispersion results from changes in flow diameters in the switching valve and the momentary buildup of pressure across the valve during the switching process and consequent surge in flow when the sample loop is switched into the stream. Such injection valves normally employ sliding or rotating seals in contact with the sample which result in carry-over of previous samples trapped in the seal. This results in analysis error. Further, the requirement for sliding motion across ports places certain material requirements on the valve sealing element and restricts material selection for reasons other than chemical inertness and static sealing ability. For example, PTFE polymer with its excellent chemical inertness and static sealing ability is not usually considered satisfactory for sliding seals because of its extrusion into connecting ports and subsequent shearing off of the extruded portion of the seal.

The syringe injection method of sample introduction has been modified in a variety of ways in attempts to eliminate or mitigate some of its shortcomings. For example, Special fittings and related equipment have been developed for use with syringe injection (see U.S. Pat. No. 3,346,486).

Other methods of sample introduction have also been developed. For example, in the case of micro-scale operations, the packed micro-chromatographic columns have been plugged at the end with porous plugs and samples have been imbibed into one of the porous plugs followed by solvent development through such sample loaded plug (see U.S. Pat. No. 3,692,669)

Another sample preparation procedure involves depositing drops of liquid on filter paper and some rather complicated pieces of equipment have been devised to carry out such procedures in a way that creates test specimens of acceptable quality (see U.S. Pat. No. 3,266,554)

Notwithstanding all of such prior activity and developments relative to sample introduction in chromatographic analysis procedures, additional improvements in such art are sorely needed, particularly for use in micro-scale operations in order to obtain optimum chromatographic efficiency (minimum peak width).

OBJECTS

A principal object of this invention is the provision of new improvements in liquid chromatographic methods and devices.

Further objects include the provision of:

1. New methods for introduction of substance samples into chromatography columns.

2. New devices for use in introducing substance samples into chromatography columns.

3. Improvements in the convenience and repeatability of sample introduction in chromatographic analysis.

4. New cartridges for sample introduction that are self-metering of sample volume and do not require use of a syringe for metering.

5. Such cartridges that will provide filtering of particulate matter from the sample and solvent entering the chromatographic column.

6. Sample introduction methods and devices that enhance sample concentration with a decrease in injected volume and increase in chromatographic efficiency.

7. Sample introduction devices that do not require close mechanical tolerances and high surface finishes of moving parts.

8. Sample introduction methods that permit specified pre-chemistries to be performed on the sample in-situ before introduction into the column.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The stated objects are accomplished in part in according with the invention by improvements in the manner in which substance samples are introduced into chromatography columns. Basically such new methods comprise providing a cartridge having a fluid permeable section of substantially the same cross-sectional area as the chromatographic column used in the analysis, loading the sample of the substance to be analyzed into such permeable section, placing the cartridge at the inlet end of the column with the permeable section covering the inlet end, and flowing solvent into the column through the permeable section. Preferably, cartridges for use in the invention comprise a plate, said permeable section comprises an opening through said plate and a permeable membrane covers each end of said opening. Advantageously, the space in the opening between such membranes will contain porous material.

Alternatively, cartridges of the invention may comprise a plate, said permeable section will comprise an opening through said plate and such opening is packed wih a porous plug. The plates may comprise a plurality of openings packed with porous plugs. They may be circular in shape with the openings forming a circle on the plate or the plate may be in the shape of an elongated rectangle and the openings form a longitudinal line centrally along the plate. Where the cartridges contain a plurality of fluid permeable sections, each section may be loaded with a separate sample for testing and the sections may be placed seriatum over the inlet end of the column after which solvent is flowed through each section into the column.

The stated objects are further accomplished in accordance with the invention by the provision of novel cartridges for use in sample introductions into chromatographic columns. Basically such cartridges comprise a plate formed of chemically inert material, there is a fluid permeable section in the plate having a cross-sectional area substantially the same as the cross-sectional area of the column into which a sample is to be introduced, and the fluid permeable section comprises means capable of retaining a liquid sample introduced into the permeable section and of releasing the liquid sample into a stream of solvent when solvent is passed through such section into said column. Preferably, in the new cartridges the permeable sections comprise an opening through the plate and a permeable membrane covers each end of such opening. The space in such opening between said membranes may contain porous material. Alternatively, the permeable section in the plate may comprise an opening through the plate that is packed with a chemically inert porous plug. Advantageously, the new cartridges of the invention comprise a plurality of openings packed with porous plugs. The cartridges may be circular in shape with the openings in a circular arrangment on the plate or they may be the shape of an elongated rectangle with the openings formed a longitudinal line or lines along the plate.

The objects of the invention are further accomplished by the inclusion of new sample cartridges as described above in chromatography apparatus.

BRIEF DESCRIPTION OF THE DRAWINGS

A more complete understanding of the invention may be obtained by reference to the accompanying drawings in which:

FIG. 1 is a diagrammatic illustration of apparatus comprising new improvements of the invention.

FIG. 2 is an isometric view of a new sample cartridge of the invention.

FIG. 3 is a fragmentary, cross-sectional view of one form of sample cartridge of the invention taken on the line 3—3 of FIG. 2.

FIG. 4 is a fragmentary, cross-sectional view of another form of sample cartridge of the invention.

FIG. 5 is a fragmentary, cross-sectional view of a sample cartridge of the invention positioned at the inlet end of a chromatographic column.

FIG. 6 is a fragmentary, cross-sectional view of a simple clamping mechanism for sample cartridges of the invention.

FIG. 7 is a lateral view, partly in section, showing a simple method of filling a sample cartridge of the invention.

DESCRIPTION OF PREFERRED EMBODIMENTS

Figure 8:
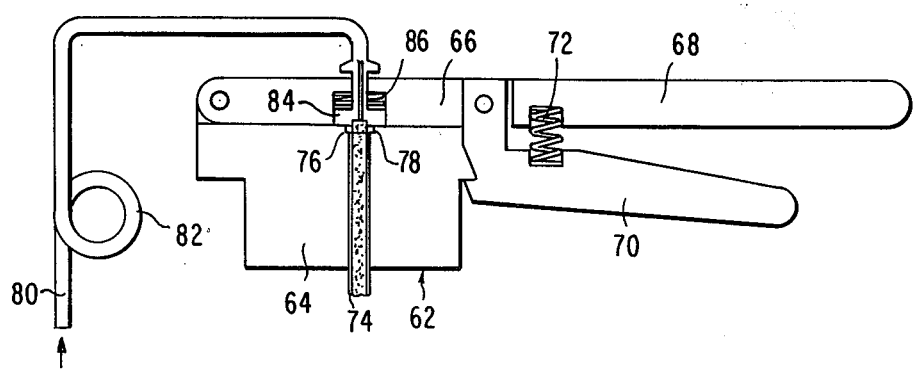
FIG. 8 is a lateral view of a single sample cartridges injector of the invention.

Referring in detail to the drawings, the chromatographic apparatus 2 comprises a separating column 4, sample injector 6, solvent delivery system 8, solvent flow line 10 and detector 12.

The sample injector 6, that constitutes a major feature of the invention, may be structured in a variety of ways. In the simple form shown in FIG. 2, the cartridge 14 comprises a plate 16 with a hole 18 through it. The two ends of the hole are covered by permeable membranes 20, the peripheral portions 22 of which are sealed in any suitable manner to the outer surfaces 24 of the cartridge 14. The plate can be made of a variety of material, e.g., metal, ceramic, plastics, etc. so long as it is chemically inert to the sample substance and the solvents to be handled in the apparatus 2. Also, the membranes 20 can be made of various materials, e.g., cellulose, plastics, etc., provided it also is chemically inert to the sample substance and the solvents. A variety of such membrane materials are commercially available and may be selected by those skilled in the construction and use of chromatographic apparatus as a result of this disclosure. The permeability of the membranes 20 should be such as to permit liquid samples to be imbibed into the space between the membranes 20 and then retained there until solvent is passed through the membranes into the column 4.

The hole 18 of cartridge 14 and all other cartridges of the invention will have a cross-section "x" substantially equal to the cross-sectional area of the column 4 with which the cartridge is to be used.

Instead of having the hole 18 between the membranes 20 unfilled before sample material is introduced therein, the cartridge 14a can have this space filled with porous material 26. Such porous material can be plastics, sintered metal, ceramic frit, etc. or individual particles of various size, e.g., several microns to several millimeters in diameter. The use of a porous structure permits an accurately manufacture physical sampling volume. A face-centered-cubic or hexagonal-close-packed alignment of spheres gives a void volume of 26 percent of the total volume of the packed space.

In the apparatus shown in FIG. 5, the outlet end 26 of the solvent flow tube 10 is fitted with a flow diffusion element 28, e.g., a wafer of porous stainless steel frit. Also, the inlet end 30 of the column 4 is fitted with a wafer 32 of porous frit to act as a retainer for the particles 34 of adsorbent material with which the column 4 is packed in accordance with established practice in operation of chromatographic columns.

The cartridge 14b of FIG. 5, comprises a solid ring 36 of inert material having its central hole filled with a plug 38 of porous material. In this embodiment, the plug 38 is formed as an integral unit and press fitted into the central hole. Such plugs can be fabricated from the types of porous materials mentioned above by pressing, sintering, fusing and similar techniques.

As shown in FIG. 5, the diameter of the central hole in cartridge 14b is equal to the diameter of the column 4. After a sample of the substance to be analyzed is introduced into the porous plug 38, the cartridge 14b is clamped between the outlet end 26 and the inlet end 30 and the wafers 28 and 32. A sliding seal is not required. The cartridge with its retained sample can be brought into contact with the inlet end of the column in a motion normal to the surface of the seal between the side walls of the cartridge and the column end. The seal material can be chosen on the basis of chemical inertness and static sealing ability and need not withstand a mechanical shearing motion across connecting ports. Positioning the cartridge in a motion parallel to the flow axis permits intimate contact of the cartridge with the inlet end 30 of the column 4 without a gap, unlike the situation for lateral motion of the sample volume in the flow stream where a gap is expedient because of mechanical tolerances and seal wear.

An important advantage of the invention is that the samples retained in the new cartridges are presented to the column in a band of substantially uniform thickness and of substantially the same diameter as the column for optimum chromatographic efficiency (minimum peak width). Also, use of a porous structure or permeable membrane provides for filtering of particulate matter from the sample and the solvent entering the column. By the use of absorbent material as the packing in the cartridge opening 18, sample concentration can be enhanced resulting in a decrease in injected volume and increase in chromatographic efficiency.

In performing an chromatographic analysis, solvent will be flowed in the direction of the arrow in FIG. 5 through the porous plug 38. The sample held in the cartridge 14b will presented to the column in a band of substantially uniform thickness and of substantially the same diameter as the column for optimum chromatographic efficiency (minimum peak width) as the sample is extracted from the cartridge 14b by the solvent flow.

The loading of a sample into the new cartridges is self-metering and does not require the use of a measuring syringe, pipette or the like. As shown in FIG. 7, a cartridge may be charged with a sample simply by dropping liquid sample material 38 onto the permeable section 40 of the cartridge 42. Capilliary action will cause the sample to load into the permeable section 40. Any excess of the material 38 will not be accepted by the cartridge. Hence, sample preparation and introduction into a column is conveniently accomplished with totally repeatable accuracy.

Other methods of loading the new cartridges may be used. For example, the cartridge may be placed in a fixture and the sample can be loaded by use of positive pressure from and syringe. Also, the cartridge can be placed in a fixture and vacuum applied by a syringe, pump or the like to one side of the permeable section to draw the sample into is from the other side. Further, the cartridge can be soaked in sample solution to load the permeable section by capillary action.

FIG. 6 illustrates s simple clamping arrangement for use with the new cartridges. The assembly 42 comprises the column 44 packed with absorbent particles 46 retained therein by the porous wafer 46. It also includes the solvent flow line 48 to which is fixed the bushing 50. The cap 52 encloses the bushing 50 and threads onto the clamp element 54 with the sample loaded cartridge 56 clamped between element 54 and bushing 50. As seen, the bottom surface of the cartridge 56 is in direct contact with the inlet end of the column 44. The plug 58 threads into the element 54 to compress the packing 60 against the column 44 to complete the sealing of the assembly 42.

FIG. 8 illustrates a single sample cartridge injector assembly 62 that is more convenient to manipulate than assembly 42. It comprises a clamp body 64 to which is pivoted the cap 66 equipped with handle 68. Latch means 70 is pivoted on the handle 68 and biased into locking position by the spring 72. The packed column 74 is sealed into the body 64 which includes a recess 76 at the inlet end of the column 74 to receive the sample loaded cartridge 78. The solvent flow line 80 includes the service loop 82 and a pressure plate 84 on its outlet end that is forced by spring 86 into contact with the top surface of cartridge 78. Cartridges can be easily inserted into the assembly 62 by releasing the latch means 70, lifting the cap 66, removing the spent cartridge 78, inserting a new loaded cartridge 78, closing the cap 66 and relocking the latch means 70.

Figure 9:
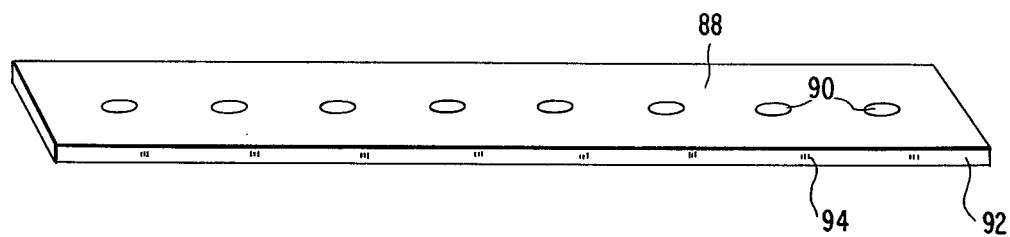
FIG. 9 is an isometric view of one form of multiple sample cartridge of the invention.

The cartridge 88 of FIG. 9 is in the form of an elongated rectangle and comprises a plurality of permeable sections 90 constructed as previously described and positioned in a longitudinal line centrally of the cartridge 88. The edge 92 of the cartridge 88 may include sample identification marks 94.

Figure 10:
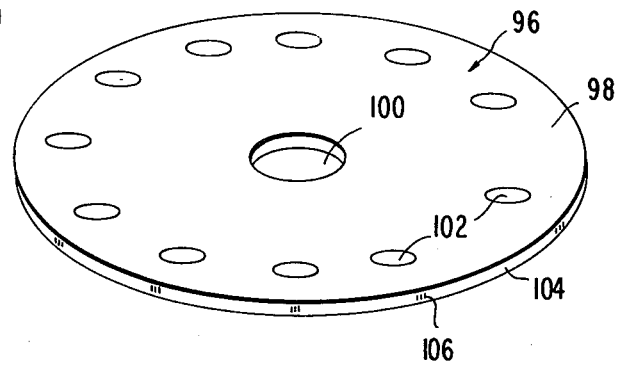
FIG. 10 is an isometric view of another form of multiple sample cartridge of the invention.

Another form of multiple sample cartridge 96 is shown in FIG. 10. It comprises a circular plate 98 with positioning hole 100 and a plurality of permeable sections of the type above disclosed aligned in a circle around the plate 98. The edge 104 of plate 98 may be provided with sample identification marks 106.

Figure 11:
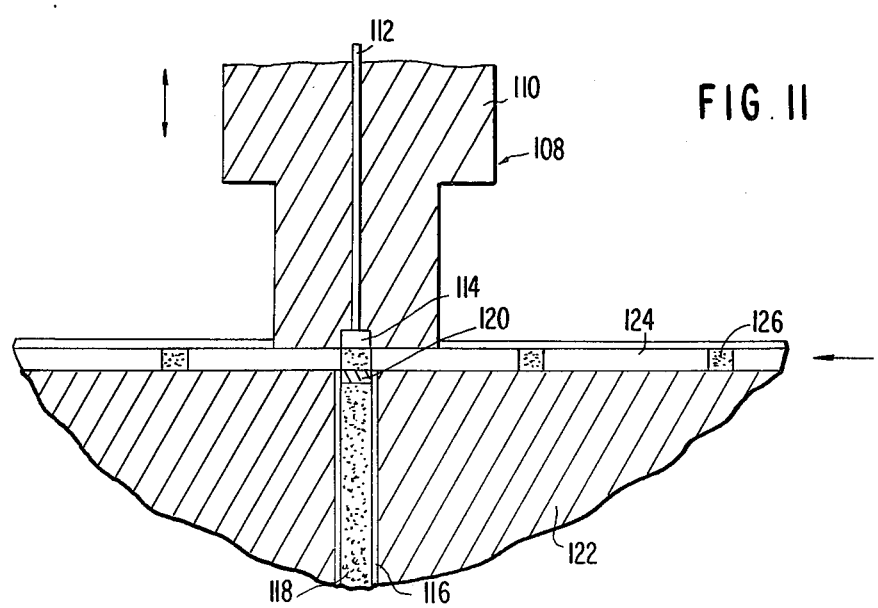
FIG. 11 is a fragmentary, sectional view of a automatic sampling device constructed in accordance with the invention.

The new multiple sample cartridges of the invention can be used in various ways in carrying out chromatographic analysis. FIG. 11 illustrates how they may be used in automatic analysis operations. The apparatus 108 comprises a pressure head 110 through which passes the solvent flow line 112 that terminates at the enlarged outlet end 114. The chromatographic column 116 packed with absorbent particles 118 that are retained in the column by the porous wafer 120 is positioned in the base 122. The cartridge 124 contains a plurality of permeable sections 126 that are imbibed with liquids samples prior to beginning an analysis run. As illustrated, the diameter of these permeable sections is equal to the diameter of the column 116. The cartridge 124 is driven by a motor (not shown) in the direction of the arrow and is indexed so that the sections 126 will be precisely positioned seriatum over the inlet end of column 116 as shown. Before such movement of the cartridge 124, the pressure head is raised, then the cartridge is indexed to move a new sample into position, next the pressure head 110 is lowered to seal the cartridge against the inlet end of the colum 116 and finally solvent is passed via line 112 through the sample section 126 into the column 116. The resulting fluid flow is then analyzed such as in the detector 12 according to established procedures.

CONCLUSION

As disclosed herein, the invention provides a new method of sample introduction into a liquid chromatograph using a cartridge having a permeable section with essentially the same cross-sectional area as that of the chromatographic column with which it is to be used. The permeable section of the cartridge is preloaded with the sample to be analyzed and this is them mechanically placed in intimate contact with the inlet end of the column with its flow axis aligned with that of the column. Solvent flow is then directed through the permeable section to sweep the sample in a uniform band into the chromatographic column for separation and analysis. The sample enters the column as a well defined plug thereby avoiding band spreading and increasing the efficiency of the analysis.

The permeable sections in the new cartridges can either be hollow with their ends that are perpendicular to the flow axis being terminated with permeable membranes to retain the sample until solvent flow is started, or the section can have a porous internal structure to hold the sample until flow is started. The porous structure of the cartridge can be chemically passive and merely serve as a reservoir for the sample, or it can be chemically active and also serve to either concentrate the sample from the material to be analyzed by adsorption or absorption or perform preparatiion chemistry on the sample, e.g., flourescence tagging for subsequent detection.

An advantage of the new devices and methods is that tight mechanical tolerances and high surface finishes of moving parts as needed in many prior known operations are not required. Also, repeated accurate metering of the sample size is obtained without need for metering syringes or the like. The invention is particularly useful in micro-scale liquid chromatography, i.e., operations that use a chromatographic column of 1 millimeter or less in diameter.

The embodiments of the invention in which an exclusive property or privilege is claimed are defined as follows:

1. In the analysis of substances by liquid chromatography, the improved method of introducing a sample of substance to be analyzed into a chromatographic column which comprises:
   providing a cartridge comprising an impervious plate having a fluid permeable section of substantially the same cross-sectional area as said chromatographic column used in the analysis,
   loading said sample of said substance into said permeable section of said cartridge,
   placing said cartridge at the inlet end of said column with said permeable section covering said inlet end and
   flowing solvent into said column through said permeable section.

2. The method of claim 1 wherein said permeable section comprises an opening through said plate and a permeable membrane covers each end of said opening.

3. The method of claim 2 wherein the space in said opening between said membranes contains chemically inert porous material.

4. The method of claim 1 wherein said cartridge comprises a plate, said permeable section comprises an opening through said plate and said opening is packed with a chemically inert porous plug.

5. The method of claim 4 wherein said plate comprises a plurality of said openings packed with porous plugs.

6. The method of claim 5 wherein said plate is circular in shape and said openings form a circle on said plate.

7. The method of claim 5 wherein said plate is in the shape of an elongated rectangle and said openings form a longitudinal line centrally along said plate.

8. The method of claim 1 wherein said cartridge contains a pluraliy of said fluid permeable sections, each section is loaded with a separate sample for testing and said sections are placed seriatum over the inlet end of said column after which solvent is flowed through each said section into said column.

9. The method of claim 1 wherein said analysis is a micro-scale liquid chromatography procedure.

10. The method of claim 1 wherein said permeable section contains porous material that is interactive with said sample substance.

11. The method of claim 10 wherein said interactive porous material enhances the sample concentration by adsorption or absorption.

12. The method of claim 10 wherein said interactive porous material produces chemical pretreatment of said sample substance.

13. The method of claim 12 wherein said interactive porous material produces chemical tagging of said sample substance.

14. A cartridge for use in introducing a substance sample into a chromatography column which comprises;
   an impermeable plate formed of chemically inert material,
   a fluid permable section in said plate having a cross-sectional area substantially the same as the cross-sectional area of said column, and
   said fluid permeable section comprising means capable of retaining a liquid sample introduced into said section and of releasing the liquid sample into a stream of solvent when said solvent is passed through said section into said column.

15. The cartridge of claim 14 wherein said permeable section comprises an opening through said plate and a permeable membrane covers each end of said opening.

16. The cartridge of claim 15 wherein the space in said opening between said membranes contains chemically inert porous material.

17. The cartridge of claim 14 wherein said permeable section comprises an opening through said plate and said opening is packed with a chemically inert porous plug.

18. The cartridge of claim 17 wherein said plate comprises a plurality of said openings packed with porous material.

19. The cartridge of claim 18 wherein said plate is circular in shape and said openings form a circle on said plate.

20. The cartridge of claim 18 wherein said plate is in the shape of an elongated rectangle and said openings form at least one line on said plate.

21. Liquid chromatographic apparatus comprising a cartridge as defined in claim 14.

22. Liquid chromatographic apparatus comprising:
   a micro-scale chromatographic column having a substantially uniform lumen throughout it length,
   a cartridge for introducing a substance sample into said column, said cartridge comprising:
   an impermeable plate formed of chemically inert material,
   a fluid permeable section in said plate having a cross-sectional area substantially the same size as said lumen of said column,
   said cartridge being positioned at the inlet end of said column with said section covering said lumen and
   means positioned in said section capable of retaining a liquid sample introduced into said section and of releasing said sample into a stream of solvent when said solvent is passed through said section into said said column.

* * * * *